(12) United States Patent
Farrell et al.

(10) Patent No.: US 6,511,420 B1
(45) Date of Patent: Jan. 28, 2003

(54) VIDEO OPTO-DIAGNOSTIC INSTRUMENT WITH SINGLE-ADJUSTMENT FOCUS

(75) Inventors: Richard A. Farrell, Laurel, MD (US); Lorenz J. Happel, Jr., Ellicott City, MD (US); Russell L. McCally, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/370,646

(22) Filed: Aug. 6, 1999

Related U.S. Application Data

(60) Provisional application No. 60/095,534, filed on Aug. 6, 1998.

(51) Int. Cl.[7] .............................. A61B 1/04; A61B 3/00
(52) U.S. Cl. ..................... 600/167; 600/162; 600/200; 351/205
(58) Field of Search .................................. 600/112, 113, 600/162, 163, 165, 167, 199, 200; 348/73, 75; 351/205

(56) References Cited

U.S. PATENT DOCUMENTS

| | | | | |
|---|---|---|---|---|
| 4,153,834 A | * | 5/1979 | Hayamizu | .................... 250/201 |
| 4,449,798 A | * | 5/1984 | Nohda | ......................... 351/207 |
| 4,659,187 A | * | 4/1987 | Tsuji et al. | .................. 359/688 |
| 4,905,082 A | * | 2/1990 | Nishigaki et al. | ........... 600/109 |

* cited by examiner

*Primary Examiner*—John P. Leubecker
(74) *Attorney, Agent, or Firm*—Francis A. Cooch

(57) ABSTRACT

A hand-held ophthalmoscope modified by the removal or augmentation of the focusing wheel and the addition of a manual or automatic focusing lens system. An electronic imager (CCD array or video camera) is placed optically conjugate to a viewing screen such that focus operations performed by the examiner to adjust the image seen by the examiner on the screen also focuses the image on the electronic imager. This is accomplished by an optical system which includes a straight path from the viewing screen to the patient's eye with a beam splitter interposed to cause the image of the patient's eye to be reflected onto the imager. As a result, when the examiner uses the focusing lens system, manual or automatic, positioned between the beam splitter and the patient's eye, to affect the image viewed by the examiner, the focus of the imager is simultaneously affected as well. Alternatively, the image from the imager is sent to a liquid crystal display (LCD) in the instrument's eye piece; when the examiner focuses the image on the LCD, the image on the imager is focused simultaneously. Also provided is an automatic focusing system for the imager that operates independently of the examiner's focusing adjustments. An automatic focusing system for the imager can also be incorporated in the other two embodiments. The output from the electronic imager can be in digital or analog form and can consist of a single frame or a video stream.

22 Claims, 3 Drawing Sheets

VIDEO OPTO-DIAGNOSTIC INSTRUMENT WITH SINGLE-ADJUSTMENT FOCUS

CROSS-REFERENCE TO RELATED APPLICATION

This application claims the benefit of prior filed copending U.S. provisional application serial No. 60/095,534, filed Aug. 6, 1998.

BACKGROUND OF THE INVENTION

1. Field of the Invention

This invention relates generally to medical diagnostic instruments and, more specifically, to a hand-held opto-diagnostic instrument, e.g., an ophthalmoscope or an otoscope, modified so that a video image generated by the instrument is in proper focus. In some embodiments, fine focus adjustments performed by an examiner (physician or physician's assistant), or automatically by the instrument for the examiner, simultaneously focus the video image generated by the instrument. The invention also includes apparatus for automatically fine focusing the video image independently of the examiner.

2. Description of the Related Art

Various hand-held opto-diagnostic instruments for use by a physician during office examinations of a patient have been known in the art for many years. Such handheld instruments include the direct ophthalmoscope (for examination of the eye). Physicians assistants or nurses can readily be trained to use these instruments.

Direct ophthalmoscopes provide a source of illumination for the retina and a small peephole for the examiner to view the fundus of the eye. Such instruments also incorporate a focusing wheel which has a series of positive and negative lenses (usually in one diopter steps) which correct for the physician's and patient's eye. Fine focus (i.e., in the ±½ diopter range between steps) is achieved via the examiner's accommodation, i.e., by changes in the ocular lens of the examiner's eye.

Currently available direct ophthalmoscopes modified for video and telemedicine make use of two separate focusing mechanisms. The first is the standard focusing wheel discussed above. A beam splitter is placed after the focusing wheel which directs part of the beam through the second mechanism, a continuous focus lens, which images the patient's retina on a CCD array. This lens is adjusted by viewing a distant object through the ophthalmoscope and focusing the object's image on a television viewing screen. As the examiner observes different regions of the patient's retina, fine focus is achieved via the examiner's accommodation exactly as in a standard direct ophthalmoscope, but the focus of the image on the CCD is not similarly corrected unless done manually through the continuous focus lens.

U.S. Pat. No. 5,239,984 to Cane et al discloses employing video technology in combination with hand-held diagnostic medical instruments through the use of an adapter which is removably secured to the instrument. The adapter utilizes a beam splitter which provides two optical outputs. One of the optical outputs goes to the medical system eyepiece to enable the examiner to obtain a direct view of the target area, such as the retina of the eye. The second optical output goes to a video camera head, typically a solid state imager such as a charged-coupled device (CCD). This allows for video output of the target area for use in producing hard copy photographs, real time video display, or telecommunication links to remote video hook-ups.

As noted above, one difficulty experienced in the use of such instruments is that focusing the image requires separate adjustments for the two different images. Many devices make use of two separate focusing mechanisms. As the examiner observes different parts of the patient's retina, fine focus is achieved via the examiner's accommodation exactly as in a direct ophthalmoscope, but the focus of the image on the CCD is not similarly corrected. Thus, the image on the CCD must be focused using a separate focusing mechanism.

U.S. Pat. No. 5,599,276 to Hauptli et al discloses a hand-held device with a video adapter coupled into the line of sight between the operator and a diopter indicator window. Hauptli's device is arranged so that the operator may view the diopter indicator window while the video adapter is coupled into the instrument by use of mirrored reflectors, such as a prism. The focus adjustments are made by an adjustment means between the video adapter and a patient's eye; however, no details are given for how the image on the video monitor is focused. The primary purpose of Hauptli's device is to display the diopter setting of the lens in the focusing wheel to the physician while he is viewing through the ophthalmoscope.

Other devices may make focus refinements solely by using the image of the CCD. For example, U.S. Pat. No. 5,125,730 to Taylor et al discloses a fundus imaging device (a hand-held fundus camera) which utilizes a CCD combined with a focusing means to provide an image of the patient's eye on a video display device.

However, none of the above devices assure that the image viewed by the examiner is in fine focus on the CCD array or other imaging device. Such a capability would be beneficial because it would save the time and expense of having to deal with separate fine focus systems for the examiner and the CCD array. Also, the examiner would be assured that fine focus adjustments made to affect the examiner's image also affect the fine focus of the CCD array.

SUMMARY OF THE INVENTION

A hand-held ophthalmoscope is modified by replacing or augmenting the focusing wheel with a manual or automatic focusing lens system which provides coarse and fine focus. In one embodiment, an imager, such as a CCD array or video camera, is placed optically conjugate to a viewing screen analogous to that used in single lens reflex (SLR) cameras such that focus operations performed by the examiner to adjust the fine focus of the image on the viewing screen also fine focuses the image on the CCD array or video camnera. The viewing screen can also incorporate a focusing aid such as, but not limited to, microprisms.

In this embodiment, the invention operates by using an optical system which includes a straight path from the patient's eye to the viewing screen with a beam splitter interposed to cause the image of the patient's eye to be reflected onto the CCD array or video camera while the image is also passed through onto the viewing screen. As a result, when the examiner uses the focusing lens system, manual or automatic, positioned between the beam splitter and the patient's eye, to affect the image seen on the screen, the focus of the CCD array or video camera is simultaneously affected as well.

In an alternate embodiment the image from the CCD array is sent to a liquid crystal display (LCD) which is substituted for the viewing screen. The examiner, who does not directly view the patient's eye, focuses the image on the LCD which automatically and simultaneously focuses the image output from the CCD array.

In still another embodiment a novel automatic focusing system, focuses the output of the CCD array independently of the examiner.

The image on the CCD array can be output in digital or analog form. If a video camera is used, the image is output in standard (analog) video format.

Several objects and advantages of the present invention are:

(a) to eliminate the examiner's accommodation as an adjustable optical element other than to bring the real image on the viewing screen into sharp focus;

(b) to provide an ophthalmoscope that assures that the CCD or video camera image is in fine focus; and (c) to provide an ophthalmoscope that has an image capture switch, thus allowing the examiner to save the in-focus image that is directly viewed through the ophthalmoscope.

DETAILED DESCRIPTION OF THE INVENTION

Figure 1:
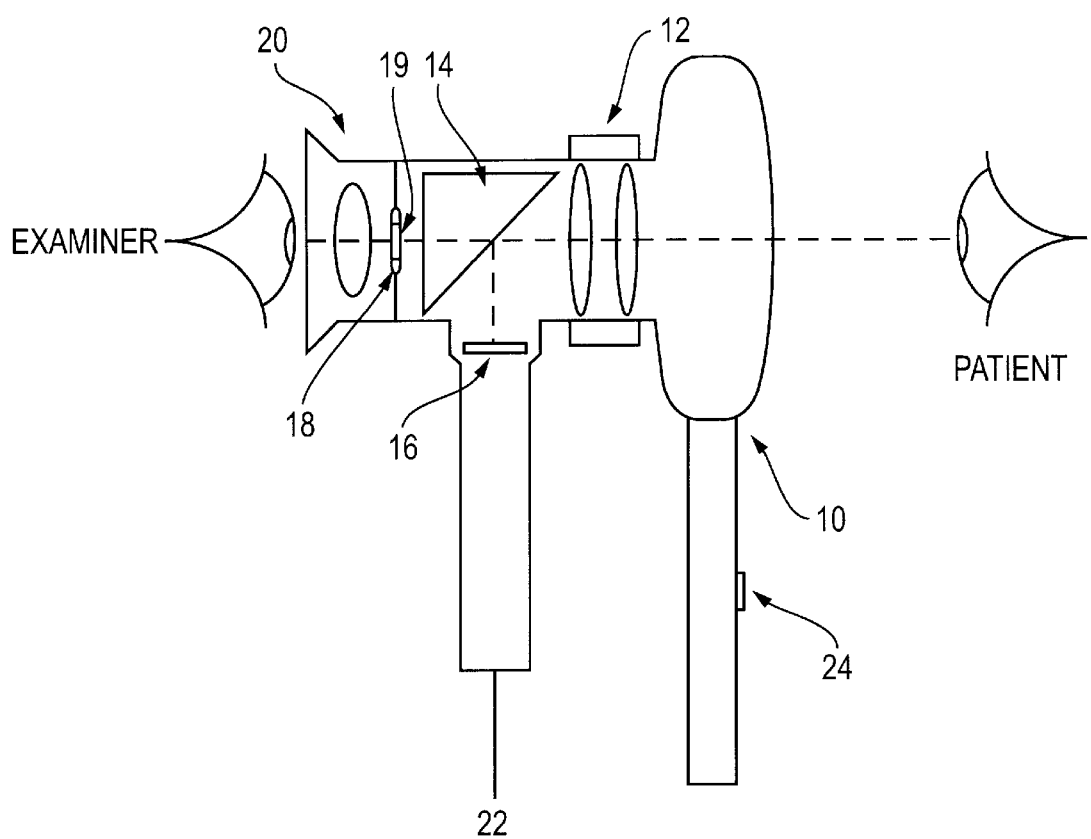
FIG. 1 is a schematic illustrating the components of the modified ophthalmoscope of the invention.

Referring to FIG. 1, a direct ophthalmoscope 10 has been modified by adding a continuously variable focusing lens (with either manual or automatic focus adjustment) to provide fine focus. This lens, together with the coarse focus provided by the focusing wheel comprises a lens system 12 which is located between a beam splitter 14 and the patient's eye. The lens system 12 forms a first real image of the retina on an imager 16, e.g., a CCD array or video camera, via the beam splitter 14. The light passing directly through the beam splitter 14 forms a second real image on a viewing screen 18 which is located conjugate (i.e., in the equivalent optical position) to the imager 16. The viewing screen is analogous to that used in SLR cameras.

The second real image is viewed by the examiner through a magnifying eyepiece lens 20 and focused by the continuously variable focusing or auto-focusing lens system 12. The invention allows the incorporation of a focusing aid in the viewing screen 18 such as, but not limited to, a microprism device 19. Because the viewing screen 18 is optically conjugate to the imager 16, the invention ensures that the first real image on the imager 16 is always in focus when the second or directly observed (by the examiner) real image is in focus on the viewing screen 18.

Figure 2:
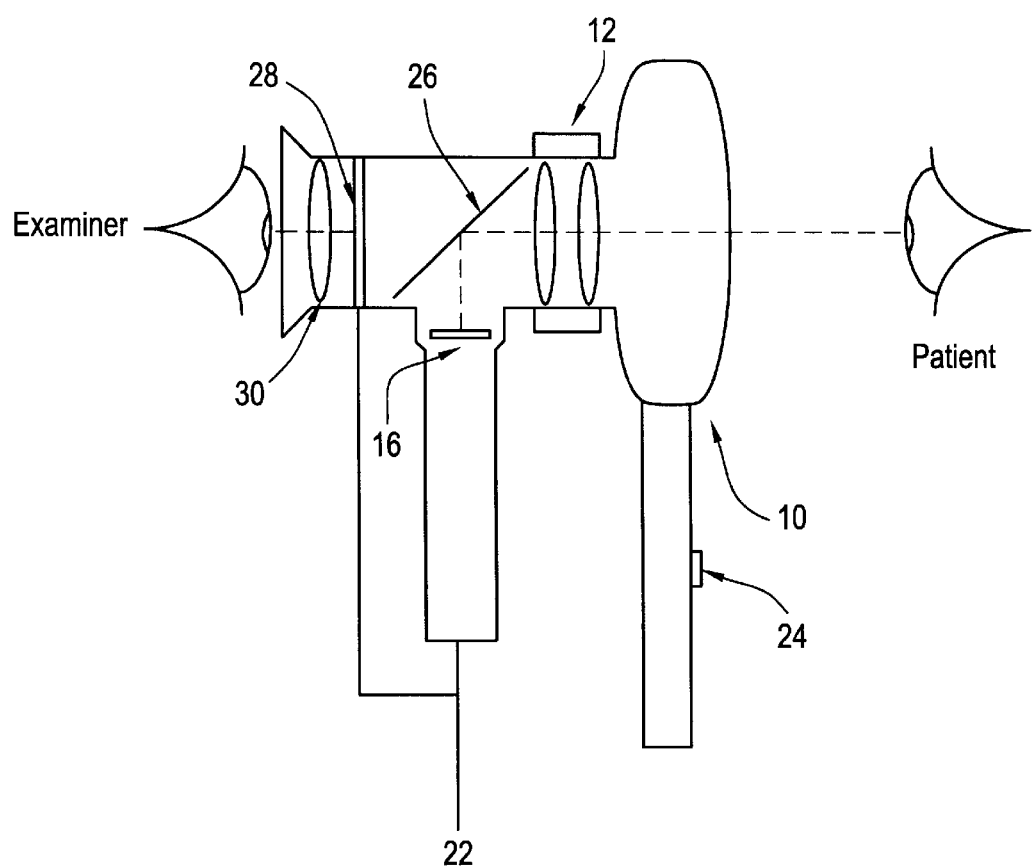
FIG. 2 is a schematic illustrating the liquid crystal display embodiment of the invention.

In a second embodiment, as shown in FIG. 2, the examiner is able to view the output of the imager 16 directly. This is accomplished by replacing the beam-splitter assembly with a simple folding mirror 26 and mounting a miniature liquid crystal display (LCD) 28 and display viewing optics 30 where the physician would ordinarily place his eye on the ophthalmoscope. The light from the patient's eye is reflected by mirror 26 to form a first image on imager, 16, e.g., a CCD array. The output of the imager 16 is then sent to the LCD 28 to form a second image. Thus, the examiner by viewing the second image will be able to see the quality of the first image captured by the imager 16 and can compensate for poor image quality by adjusting the focus using lens system 12. Thus, the examiner is able to focus both first and second images simultaneously. The fine focus of lens system 12 can be automated.

Figure 3:
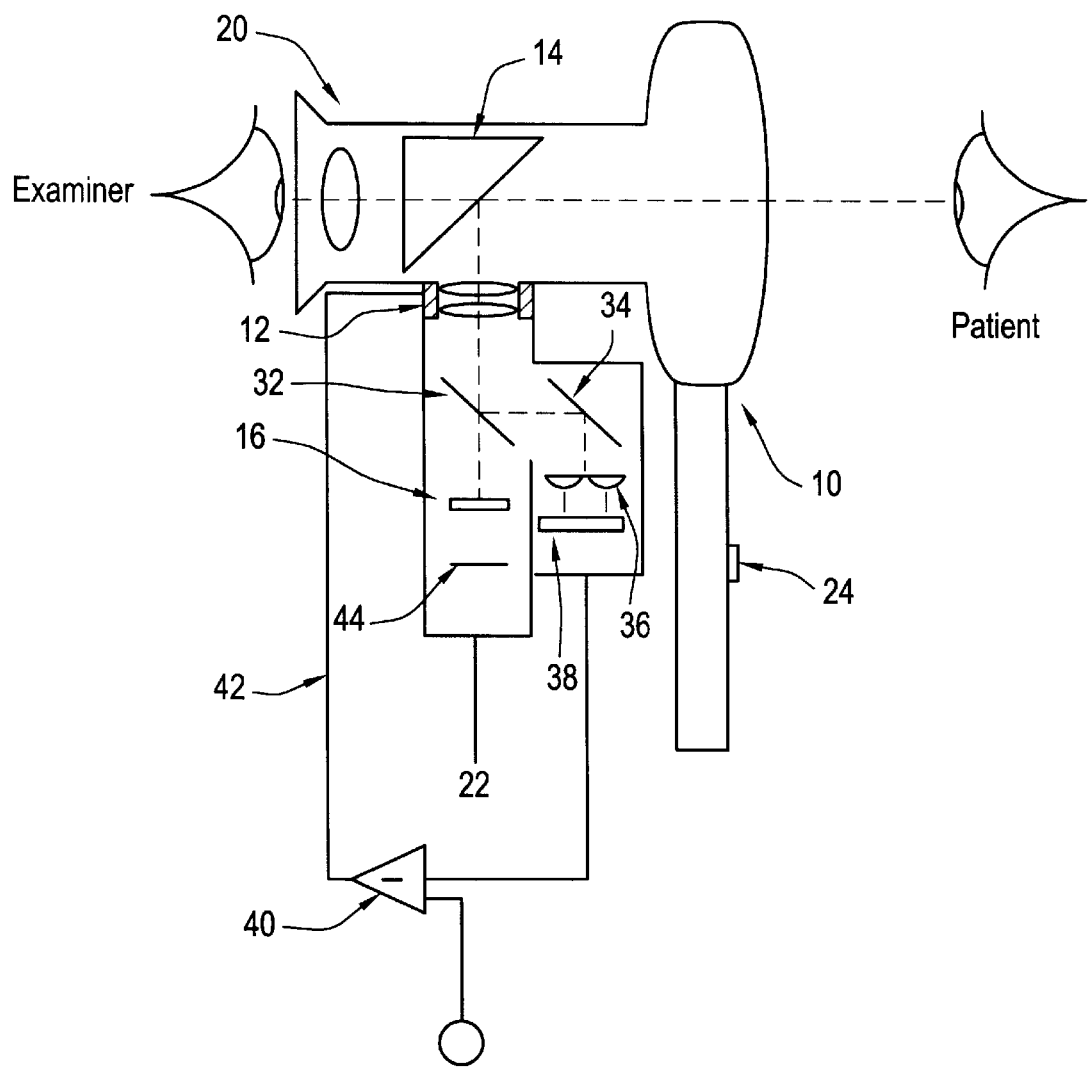
FIG. 3 is a schematic illustrating an embodiment of the invention containing an additional optics/detection system for automatic focusing independently of the examiner.

In a third embodiment as shown in FIG. 3, an additional optics/detection system is incorporated to effect an automatic focusing thus relieving the physician of the focusing operation for the imager 16. The lens system 12, minus the focusing wheel (not shown separately) which remains in its original position, has been moved although it could be retained in its original position as shown in FIGS. 1 and 2. The beam splitter allows the examiner to view the patient's eye directly while also causing light to pass through the lens system 12 and a partial reflector 32 to form a first image on CCD 16. The partial reflector also sends light to mirror 34 which sends the light through lenslet array 36 to form a second image on a linear CCD array 38. The output from the linear CCD array is then sent through a difference amplifier 40 to form an error signal which is sent to lens system 12 through feedback loop 42. Such a system will judge if the image is sharp (in focus) based upon well-understood in the art image quality criterion. As noted, an error signal, derived from the criterion, will be used to actively focus the first image on the imager 16 by adjusting the position of the lens system 12.

Alternatively, autofocus could be accomplished by deriving image quality in integrated circuit 44 based on the image received from imager 16. The integrated circuit 44 outputs a signal indicative of the quality of the first image to difference amplifier 40. Amplifier 40 then forms an error signal indicative of focus error which is sent to lens system 12, through feedback loop 42 causing the lens system 12 to automatically focus the first image. In this embodiment, partial reflector 32, mirror 34, lenslet array 36, and linear CCD array 38 would not be required. Clearly, automated fine focusing systems based on analyses of the CCD image could be incorporated into embodiments 1 and 2.

Below the imager 16, in any of the embodiments, there is a direct digital or analog output 22. The digital output used in conjunction with a CCD would provide the highest quality. The digital output thus lends itself to storage in a digital storage medium, such as a computer hard drive or digital camera memory card. An image capture switch 24 located on the handle allows the image on the screen (digital frame) to be saved to a digital storage medium for later use. The digital storage medium could either be incorporated directly into the modified ophthalmoscope, or connected externally as part of, e.g., a computer. Additionally, the real-time analog video, such as National Television Systems Committee (NTSC), can be generated from the digital data. This signal could be used for the recording or transmission of the images for instructional purposes and/or video-based examination (i.e. telemedicine applications.)

The present invention allows focus operations to be performed manually by the examiner using a continuously variable focusing system, or automatically if an auto-focusing system is used, to simultaneously focus the image on the imager 16 and the viewing screen 18. The embodiments in FIGS. 1 and 2 also provide the examiner with "what you see is what you get" viewing; that is, while looking directly through the ophthalmoscope, the examiner knows the focus details of the image that is being outputted and captured. The image capture switch 24, coupled with the focusing lens system 12, allows the examiner to save the exact image that is being viewed through the ophthalmoscope. Alternatively, the imager 16 can send the image to an LCD in the instrument eye piece which when focused by the examiner causes the image output from the imager to be focused too. In another embodiment, automatic focusing means operating independently of the examiner relieves the examiner of having to worry at all about focusing the image from the imager. Direct digital output of the image on the CCD array ensures the image is of the highest quality possible. Analog output from the CCD or a video camera can also be used. Similar considerations apply to indirect ophthalmoscopes and the same principles for eliminating examiner accommodation would apply. The invention can be applied to other opto-diagnostic instruments, as well, for example, an otoscope, an instrument for inspecting the ear. In the case of the otoscope, the invention would be similar to the device shown in FIG. I except that the patient's eye would be replaced with the patient's ear and the instrument would have a cone shaped, disposable ear speculum attached to it on into the ear.

We claim:

1. Apparatus in an opto-diagnostic instrument used by a medical examiner for simultaneously focusing first and second images of an original image of an area of interest comprising:

a beam splitter for splitting the original image into the first and second images;

a lens system located between the beam splitter and the area of interest for focusing the first and second images;

an imager for receiving the first image; and a viewing screen located optically conjugate to the imager for receiving the second image for direct observation by the examiner;

wherein, when the second image on the viewing screen is focused using the lens system, the first image on the imager is thereby focused simultaneously.

2. The apparatus as recited in claim 1 further comprising means for outputting a signal from the imager, the signal representing the first image.

3. The apparatus as recited in claim 2, further comprising switch means for saving the first image.

4. The apparatus as recited in claim 2, wherein the signal is digital.

5. The apparatus as recited in claim 2, wherein the signal is analog.

6. The apparatus as recited in claim 1, wherein the opto-diagnostic instrument is an otoscope.

7. The apparatus as recited in claim 1, wherein the imager is a charge-coupled device.

8. The apparatus as recited in claim 1, the lens system including a single continuously variable focusing system.

9. The apparatus as recited in claim 1, the lens system including an auto-focusing system.

10. A method for simultaneously focusing first and second images of an original image of an area of interest in an opto-diagnostic instrument comprising the steps of:

splitting the original image into first and second images;

forming the first image on an imager and the second image on a viewing screen, the viewing screen being located conjugate to the imager; and focusing the second image on the viewing screen using a lens system, the lens system simultaneously focusing the first image on the imager.

11. The method as recited in claim 10, further comprising the step of outputting a signal from the imager, the signal representing the first image.

12. The method as recited in claim 11, wherein the outputted signal can be saved by activating a switch means.

13. The method as recited in claim 10, wherein the imager is a charge-coupled device.

14. The method as recited in claim 10, wherein the opto-diagnostic instrument is an otoscope.

15. The method as recited in claim 10, wherein the lens system is single continuously variable focusing.

16. The method as recited in claim 10, wherein the lens system is auto-focusing.

17. Apparatus in an opto-diagnostic instrument used by a medical examiner for simultaneously focusing first and second images of an original image of an area of interest comprising:

a beam splitter for splitting the original image into the first and second images;

a lens system located between the beam splitter and the area of interest for focusing the first and second images;

an imager for receiving the first image;

a viewing screen located optically conjugate to the imager for receiving the second image for direct observation by the examiner; and a focusing means in the viewing screen;

wherein, when the second image on the viewing screen is focused using the lens system, the first image on the imager is thereby focused simultaneously.

18. The apparatus as recited in claim 17, the focusing means comprising a microprism.

19. Apparatus in an ophthalmoscope used by a medical examiner for simultaneously focusing first and second images of an original image of an area of interest comprising:

a beam splitter for splitting the original image into the first and second images;

a lens system located between the beam splitter and the area of interest for focusing the first and second images;

an imager for receiving the first image; and a viewing screen located optically conjugate to the imager for receiving the second image for direct observation by the examiner;

wherein, when the second image on the viewing screen is focused using the lens system, the first image on the imager is thereby focused simultaneously.

20. A method for simultaneously focusing first and second images of an original image of an area of interest in an ophthalmoscope comprising the steps of:

splitting the original image into first and second images;

forming the first image on an imager and the second image on a viewing screen, the viewing screen being located conjugate to the imager; and focusing the second image on the viewing screen using a lens system, the lens system simultaneously focusing the first image on the imager.

21. Apparatus in an opto-diagnostic instrument used by a medical examiner for simultaneously focusing first and second images of an original image of an area of interest comprising:

a beam splitter for splitting the original image into the first and second images;

a lens system located between the beam splitter and the area of interest for focusing the first and second images;

an imager for receiving the first image;

a viewing screen located optically conjugate to the imager for receiving the second image; and an eyepiece lens for viewing the second image on the viewing screen;

wherein, when the second image on the viewing screen is focused using the lens system, the first image on the imager is thereby focused simultaneously.

22. A method for simultaneously focusing first and second images of an original image of an area of interest in an opto-diagnostic instrument comprising the steps of:

splitting the original image into first and second images;

forming the first image on an imager and the second image on a viewing screen, the viewing screen being located conjugate to the imager;

viewing the second image through an eyepiece lens; and focusing the second image on the viewing screen using a lens system, the lens system simultaneously focusing the first image on the imager.

* * * * *